US010675004B2

(12) United States Patent
Lundberg et al.

(10) Patent No.: US 10,675,004 B2
(45) Date of Patent: Jun. 9, 2020

(54) ULTRASOUND IMAGING APPARATUS WITH IMAGE SELECTOR

(71) Applicant: FUJIFILM SonoSite, Inc., Bothell, WA (US)

(72) Inventors: Andrew Lundberg, Woodinville, WA (US); Gina Kelly, Bothell, WA (US); Kerem Karadayi, Seattle, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 23 days.

(21) Appl. No.: 15/214,838

(22) Filed: Jul. 20, 2016

(65) Prior Publication Data

US 2018/0021022 A1    Jan. 25, 2018

(51) Int. Cl.
*A61B 8/08*    (2006.01)
*A61B 8/14*    (2006.01)
(Continued)

(52) U.S. Cl.
CPC .......... *A61B 8/5207* (2013.01); *A61B 8/0841* (2013.01); *A61B 8/14* (2013.01);
(Continued)

(58) Field of Classification Search
CPC ....... A61B 8/5207; A61B 8/0841; A61B 8/14; A61B 8/461; A61B 8/469;
(Continued)

(56) References Cited

U.S. PATENT DOCUMENTS 5,046,027 A    9/1991    Taaffe et al.
5,274,759 A    12/1993    Yoshioka et al.
(Continued)

FOREIGN PATENT DOCUMENTS

WO    2004093687    11/2004
WO    2015166377    11/2015

OTHER PUBLICATIONS

International Searching Authority, International Search Report and Written Opinion, PCT Patent Application PCT/US2017/042647, dated Sep. 18, 2017, 13 pages.
(Continued)

*Primary Examiner* — Sanjay Cattungal
(74) *Attorney, Agent, or Firm* — Womble Bond Dickinson (US) LLP (57) ABSTRACT

An ultrasound imaging system includes a cine buffer in which image frames produced during an examination are stored. A processor is programmed to select one or more image frames from the cine buffer for presentation to an operator for approval and inclusion in a patient record or other report. The operator can accept the proposed image frames or can select one or more other image frames from the cine buffer. The processor may select image frames at spaced intervals in the cine buffer for presentation. Alternatively, the processor compares image frames in the cine buffer with one or more target image frames. Image frames that are similar to the target image frames are presented to the operator to confirm. Alternatively, image frames can be selected by the processor that contain a specific feature or that are similar to image frames that were previously selected by the operator when performing a particular type of examination.

10 Claims, 3 Drawing Sheets

(51) Int. Cl.
*A61B 8/00* (2006.01)
*G01S 7/52* (2006.01)
*G06K 9/62* (2006.01)
*G06T 1/60* (2006.01)
*G06T 7/00* (2017.01)
*A61B 17/34* (2006.01)

(52) U.S. Cl.
CPC .............. *A61B 8/461* (2013.01); *A61B 8/469* (2013.01); *G01S 7/52034* (2013.01); *G01S 7/52085* (2013.01); *G06K 9/6201* (2013.01); *G06T 1/60* (2013.01); *G06T 7/0012* (2013.01); *A61B 2017/3413* (2013.01); *G01S 7/52098* (2013.01); *G06K 2209/051* (2013.01); *G06T 2207/10132* (2013.01); *G06T 2207/30004* (2013.01)

(58) Field of Classification Search
CPC ......... A61B 2017/3413; G01S 7/52034; G01S 7/52085; G01S 7/52098; G06K 9/6201; G06T 1/60; G06T 7/0012; G06T 2207/10132; G06T 2207/30004
USPC .................................................. 600/437–469
See application file for complete search history.

(56) References Cited

U.S. PATENT DOCUMENTS

| | | | |
|---|---|---|---|
| 6,086,539 A | 7/2000 | Guracar et al. | |
| 6,126,599 A * | 10/2000 | Jago | G01S 7/52025 600/437 |
| 6,213,945 B1 * | 4/2001 | Tynan | A61B 8/06 600/441 |
| 6,217,515 B1 | 4/2001 | Yamakawa | |
| 6,231,508 B1 | 5/2001 | Miller et al. | |
| 6,524,246 B1 * | 2/2003 | Kelly | A61B 8/0825 600/437 |
| 7,645,238 B2 * | 1/2010 | Hirsh | A61B 8/12 600/437 |
| 7,931,594 B2 * | 4/2011 | Hirsh | A61B 8/12 600/437 |
| 9,177,110 B1 * | 11/2015 | Fram | G06F 19/321 |
| 2002/0035326 A1 | 3/2002 | Kamiyama | |
| 2004/0225221 A1 * | 11/2004 | Olsson | A61B 8/08 600/447 |
| 2004/0267122 A1 * | 12/2004 | Nadadur | A61B 8/08 600/440 |
| 2007/0016029 A1 * | 1/2007 | Donaldson | A61B 5/7475 600/437 |
| 2009/0299182 A1 * | 12/2009 | Asafusa | A61B 8/481 600/443 |
| 2010/0036248 A1 | 2/2010 | Chouno | |
| 2012/0078097 A1 * | 3/2012 | Wang | A61B 8/483 600/437 |
| 2012/0253181 A1 | 10/2012 | Okamura | |
| 2013/0190600 A1 | 7/2013 | Gupta et al. | |
| 2013/0345563 A1 * | 12/2013 | Stuebe | G01S 7/52084 600/440 |
| 2015/0005637 A1 | 1/2015 | Stegman et al. | |
| 2016/0173770 A1 * | 6/2016 | Fosodeder | A61B 8/5207 348/77 |
| 2017/0124701 A1 * | 5/2017 | Liang | A61B 8/0858 |

OTHER PUBLICATIONS

PCT International Preliminary Report on Patentability for PCT/US2017/042647 dated Jan. 31, 2019.
Extended European Search Report for Application No. 17831711.1, dated Jan. 20, 2020, 12 pages.

* cited by examiner

ULTRASOUND IMAGING APPARATUS WITH IMAGE SELECTOR

TECHNICAL FIELD

The disclosed technology relates to ultrasound imaging systems, and in particular to systems for improving workflow within clinical settings using ultrasound imaging systems.

BACKGROUND

In ultrasound imaging, an operator of a system uses a probe to obtain ultrasound images of a patient. The images captured by the system may be viewed, printed or included in a patient report for diagnosis and record keeping. In addition, select images may be included in a report that is used to bill the patient or their insurance for the services rendered.

Depending on the examination procedure being performed, the number and subject of the images required in a report of the examination may be standardized or defined. For example, an internal exploratory scan may require that images of the patient's liver, bladder, intestines, kidneys and stomach be obtained. Similarly, a pre-natal scan may require images and measurements of various anatomic structures of a fetus. In a typical single operator examination, a physician or an ultrasound technician uses the imaging system to obtain all the images needed to complete the examination. These images are typically selected by the user during the exam, stored in a buffer memory and must be reviewed after the examination is complete to mark or otherwise identify images to be used in creating a record of the scan. In the case of a procedure, such as an ultrasound-guided regional anesthesia injection, where the care provider cannot stop mid procedure or has no free hands to control the system, a second person may assist in controlling the system settings and collecting the needed images during the procedure.

SUMMARY

To improve on the systems described above, the disclosed technology relates to an imaging system that includes a cine buffer memory to store image frames as they are produced by the imaging system. A processor analyzes the image frames stored in the cine buffer and presents one or more selected image frames to the operator for approval. In one embodiment, the image frames selected are image frames that are obtained at equal time intervals during the examination. Alternatively, the image frames may be selected by comparing the image frames in the cine buffer with one or more target image frames. The target image frames may be determined by the type of scanning procedure being performed, based on previous operator selections when performing the same or similar type of scanning procedure. In another embodiment, image frames that are presented are selected by determining whether the image frames meet a particular quality metric, such as where a measurement is most clearly seen or image frames that contain a particular anatomical structure or interventional instrument (e.g., a needle), or are obtained at a particular point in an examination procedure. In one embodiment, image frames are selected for presentation based on how different the image frames are from previous image frames stored in the cine buffer.

A programmed processor in the imaging system allows an operator to approve the selection of one or more of the presented images for inclusion in a report or summary of the scanning procedure. Alternatively, the operator can select their own images by, for example stepping through and selecting one or more image frames stored in the cine buffer. Optionally, the operator can make measurements on these selected image frames before storing them depending on the clinical protocol for the targeted exam/procedure.

DETAILED DESCRIPTION

As described above, the disclosed technology relates to imaging systems and in particular to ultrasound imaging systems. In some described embodiments, an ultrasound imaging system includes a programmed processor that is configured to select one or more image frames that are captured during an examination of a patient. An operator can approve the selected image frames or can choose alternative image frames. Once the image frames are approved, the processor can mark or otherwise designate the approved image frames for inclusion in a report of the examination for the patient's records and/or for billing purposes. Although the disclosed technology is illustrated in connection with an ultrasound imaging system, it will be appreciated that the technology can be employed with other types of imaging systems such as, but not limited to, MRI systems, video endoscopy systems or other medical imaging systems that capture many images during an examination procedure.

Figure 1:
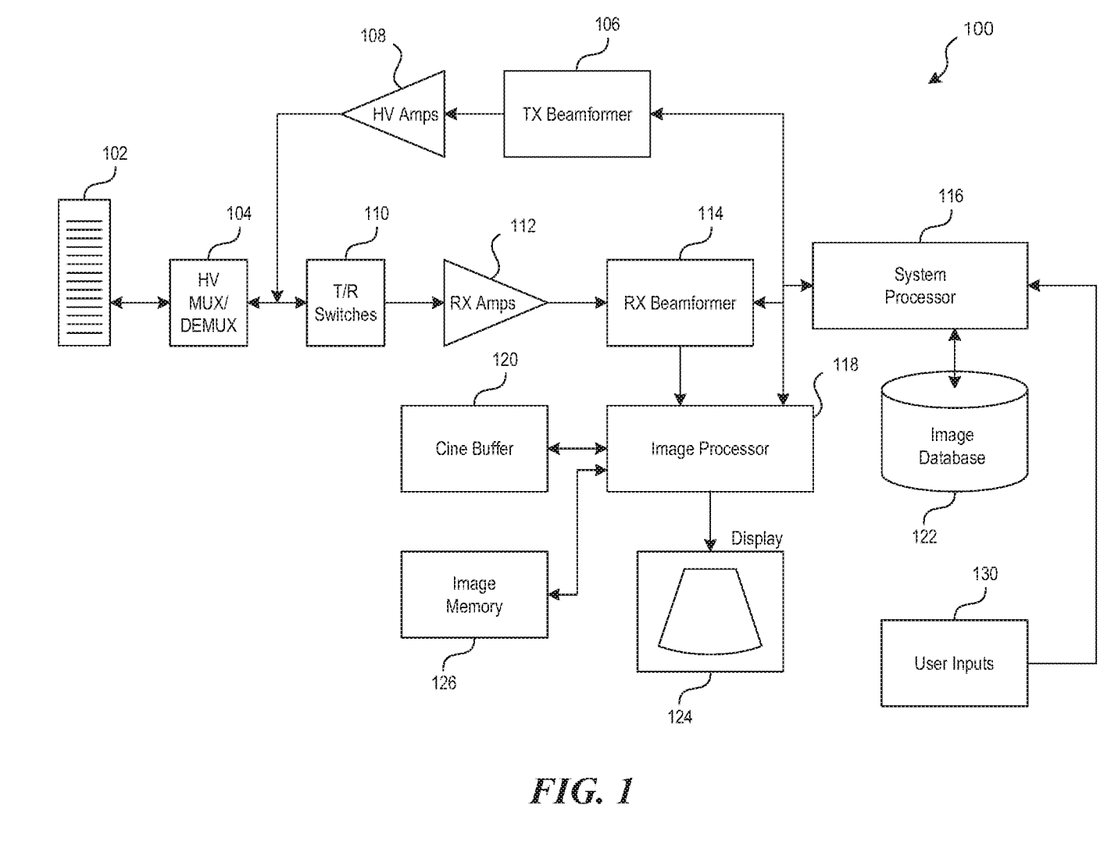
FIG. 1 illustrates a block diagram of an ultrasound imaging system in accordance with one embodiment of the disclosed technology.

As shown in FIG. 1, a simplified block diagram of an ultrasound imaging system 100 includes a transducer 102 that is configured to send ultrasound signals into a body and to detect the corresponding echo signals. The transducer 102 may be a single-element transducer or may consist of one- or two-dimensional linear or phased array of transducer elements. The transducer 102 may be connected to a high voltage multiplexer/de-multiplexer (HV mux/demux) 104 that is used select individual or groups of transducer elements in the transducer 102. In the case of a phased-array, signals to be transmitted by the transducer 102 are generated by a transmit beamformer 106 that adjusts the timing of the signals in order to direct the signals in a particular direction and to focus the signals at a particular depth in the tissue. Alternatively, unfocused (plane) waves can be transmitted by the transducer. Signals from the transmit beamformer 106 are amplified by one or more high-voltage amplifiers 108 before being applied to the HV mux/demux 104 and the transducer 102.

A transmit/receive (T/R) switch 110 operates to disconnect the receive electronics of the ultrasound system from the transducer when the higher powered transmit pulses are being transmitted. The T/R switch 110 is closed when the imaging system is to detect the returning echo signals. Signals received by the T/R switch 112 are amplified by low-noise receive amplifiers 112 that implement a gain function that typically varies according to the depth from which the echo signals originate. For a directional ultrasound system, the outputs of the receive amplifiers 112 feed a receive beamformer 114 that delays and sums the amplified received echo signals. In most ultrasound systems, the analog received signals are converted to corresponding digital signals, after amplification, with a number of analog to digital converters (not shown) that are positioned between the receive amplifiers 112 and a receive beamformer 114 in the signal path.

In one embodiment, a system processor 116, which could be implemented as one or more programmed microprocessors, is configured to execute program instructions that are stored in an internal or external computer readable memory (not shown) to control the operation of the ultrasound imaging system.

Beamformed ultrasound signals produced by the receive beamformer 114 are delivered to an image processor 118. The image processor 118, which may include one or more general purpose microprocessors (including the system processor 116), one or more digital signal processors (DSP), one or more graphics processor units (GPU), application-specific integrated circuits (ASIC) or the like, converts the raw, beamformed signals into a two-dimensional image frame of pixel data that can be stored in memory and shown to an operator on a video monitor or other display 124. The image frames produced by the image processor 118 are stored in a buffer memory 120 (also known as a cine buffer), which in one embodiment is operated as a circular buffer of memory elements that stores a select number of frames as they are produced during an examination. In one embodiment, the cine buffer 120 can store 2-5 minutes of data at 30 frames/sec or 3600-9000 image frames of ultrasound data or more. In one embodiment, once the cine buffer 120 is full, the oldest image frame in the buffer is overwritten with a new image frame in a circular fashion. A memory 126 is used to store the image frames for archival purposes. The contents of the memory 126 may be transferred to a remote patient records keeping system after an examination is complete. In some embodiments, at least some of the image frames that are stored in the memory 126 are compressed to save space and therefore may lack some detail compared with the image frames that are stored in the cine buffer 120.

A number of operator inputs 130 such as keys, buttons, knobs, voice commands, gestures or software-configured controls, such as touch screen controls or the like, allow an operator to change the operating characteristics of the ultrasound machine and to input commands to the system processor 116.

In one embodiment, an operator begins an ultrasound examination procedure by using the input controls 130 to select an examination type from a number of pre-defined examination procedures that are shown on the display 124 or may have a dedicated control on a keyboard of the system. Exemplary types of examinations may include an internal organ exploratory scan, a neonatal scan, a cardiac scan, a carotid artery scan etc. Each of these scan types may be associated with particular views and measurements that are to be captured by the ultrasound machine operator. For example, a neonatal scan may require views and measurements of a baby's heart, neck tissue, femur length and other views and measurements. In one embodiment, the views and measurements required by the various examination types are stored in a knowledge base within a memory of the ultrasound system.

The operator uses a control 130 (e.g. an on-screen button, footswitch, control on an imaging probe etc.) to start the ultrasound machine capturing ultrasound image frames. These image frames are produced and stored in the cine buffer 120 until the operator uses a control 130 to halt the imaging process. As will be appreciated, the cine buffer is constructed to store several thousand image frames of ultrasound data. In the past, the operator had to review/search through all of the stored image frames to select which frames would be included in a patient's record and/or submitted for billing purposes.

To aid an operator in selecting one or more of the image frames, a processor such as the system processor 116, a DSP or a GPU executes a number of programmed instructions to analyze the image frames that are stored in the cine buffer 120 and to select one or more image frames as possible frames for review and approval by an operator. The selected image frames are displayed for the operator and the operator can either approve the selection or can select different image frames. In one embodiment, the approved image frames are marked for inclusion in a patient report of an examination, for use in billing, or both. In one embodiment, the approved image frames are stored in the memory 126 with lossless compression or with little or no compression compared to the unselected or non-approved images frames generated during the examination in order to retain more image detail.

Figure 2:
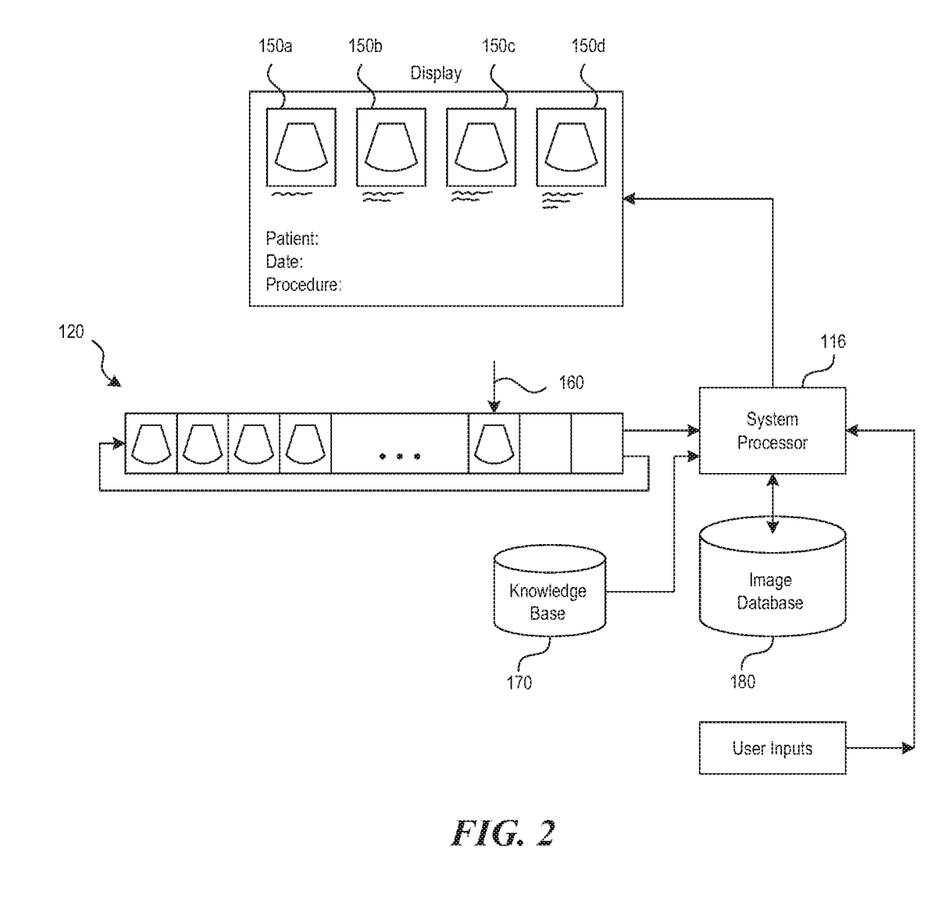
FIG. 2 illustrates a programmed processor that is configured to select image frames from a cine buffer memory for presentation to a operator in accordance with an embodiment of the disclosed technology.

FIG. 2 illustrates a display 140 in which the system processor 116 has selected and presented a number of possible image frames 150a, 150b, 150c, 150d for the operator to review and approve. The presented image frames are shown to the operator on the display 124 and operator can approve one or more of the displayed image frames for inclusion in a patient or billing report. Alternatively, the operator can select one or more other image frames for inclusion into the reports if the operator does not like the image frames that have been selected by the system processor 116. In one embodiment, the operator can view image frames that were recorded in the cine buffer near any of the displayed image frames by selecting, for example, image frame 150c on the display 124. In one embodiment, the system processor 116 determines the address of the selected image frame by for example, recalling an index pointer 160 that is associated with the image frame 150c and that indicates the address of the image frame in the cine buffer 120. The system processor then uses the determined address to recall and display a number of image frames from the cine buffer that are stored just before and/or just after the selected image frame 150c. By using an advance or rewind control on the operator inputs 130, the operator can view frames that are recorded before or after the image frame 150c. In this manner, the operator can select an image frame that may show a desired view or measurement in a way that is better or more clear than is shown in the image frame 150c that was selected by the system processor 116.

The system processor can select image frames in a number of different manners or in accordance with a number of different metrics. In one embodiment, the system processor selects image frames that are equally spaced in the cine buffer for display to the user. For example, if an examination generates 2000 image frames that are stored in the cine buffer 120, the system processor may select image frames numbered 500, 1000, 1500 and 2000 as the image frames that can be approved for possible inclusion into the patient reports. The number of frames that are initially selected may be chosen by the operator or may be defined by the procedure type.

In one embodiment, a knowledge base 170 is maintained on a computer readable media that may be internal to the ultrasound machine or may be accessible by the system processor 116 by a wired or wireless communication link.

The system processor recalls parameters from the knowledge base 170 that are associated with the examination type that is in progress. These parameters can include such things as the number of image frames to be included in a report about the procedure, the views desired in each of the image frames or the measurements desired in an image frame. For example, a nerve block procedure may require three or more different image frames to be recorded that include views of a needle approaching a target nerve, the needle at the position of the target nerve and anesthetic being delivered around the target nerve.

In one embodiment, an image database 180 is maintained on a computer readable media that may be internal to the ultrasound machine or may be accessible by the system processor 116 by a wired or wireless communication link. The image database 180 stores representative image frames that show various anatomical structures that can be compared against an image frame that is stored in the cine buffer in order to detect a match. For example, if a procedure requires an image of a patient's liver in a particular orientation, the image database 180 includes an image frame that is coded as representing a liver in a particular orientation and that is required by a particular type of examination. If the operator is performing a liver scan procedure, the system processor recalls one or more of the target image frames from the database 180 and compares the target image frames with the image frames that are stored in the cine buffer to identify those image frames that most closely match the target image frames.

In some embodiments, the target image frames are associated with narrative information about the frame. The narrative information may include the type of tissue being imaged and one or more parameters of the ultrasound machine used to obtain the image. Such parameters can include the operating mode of the ultrasound machine (B-mode, Doppler Mode, Power mode etc.) as well as power settings, pulse repetition rate, focal depth, probe used etc. The system processor can pre-populate a narrative associated with the selected image frame using the corresponding operating parameters of the ultrasound machine that were used to obtain the image frame so that the operator doesn't have to enter the narrative values manually.

In some embodiments, the processor may execute instructions that perform a machine learning algorithm to compare image frames stored in the cine buffer with image frames that were selected by the operator for a previous examination. Those image frames that bear the closest resemblance to the previously selected image frames can be presented to the operator for possible inclusion into the patient report or billing record (or other report). In this way, the processor can predict likely images that will be selected based on the user's previous actions. In some embodiments, the processor executes instructions to determine which images require measurements to be taken and cause the processor to display a graphic representing a caliper or other measurement tool on the images. The placement of the caliper graphic can be based on an image recognition of the anatomical features contained in the images. For example, an image of a femur can be analyzed and the processor can display the graphic representing the caliper along the length of the femur (or across the femur width if that is the measurement to be detected). The user can use the position of the caliper to obtain a tissue measurement or can vary the location of the caliper if they desire.

Figure 3A:
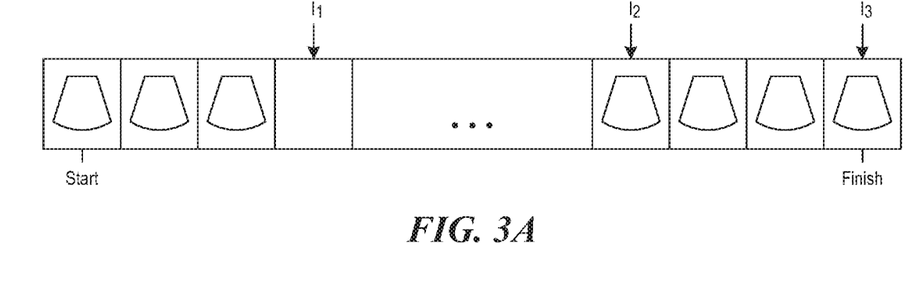
FIGS. 3A and 3B illustrate two different methods of selecting image frames from a cine buffer in accordance with the disclosed technology.
Figure 3B:
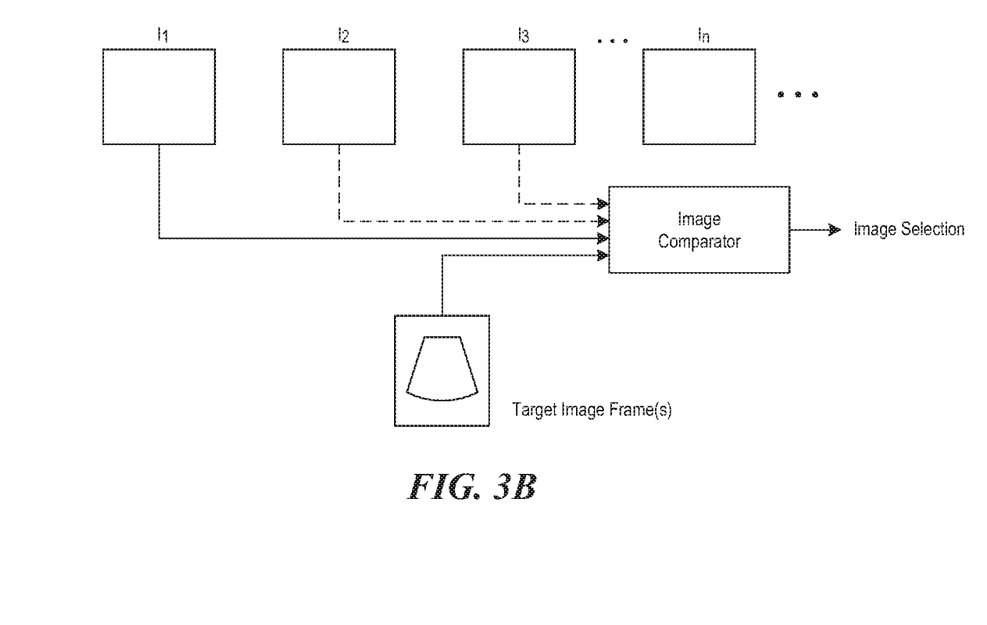

FIGS. 3a and 3b show two possible alternative methods of selecting image frames for approval by an operator of the ultrasound processing system. As shown in FIG. 3a, a cine buffer 120 stores a number of frames F1-FN that are stored when the examination first begins and continues until the examination ends. The system processor is configured to execute programmed steps to determine the number of frames stored in the cine buffer for the particular examination. In one embodiment, the system processor keeps an internal count that is increased each time an image frame is added to the cine buffer. The system processor also keeps a record of the first memory address in the cine buffer that stores a first image frame for the current examination. The desired number of image frames to be presented for approval by the operator is either received from the operator or from the parameters associated with the particular type of examination being performed. In one embodiment, the system processor divides the total number of frames stored in the cine buffer by the number of image frames desired uses the result to determine the address of the equally spaced image frames in the cine buffer. In yet another embodiment, the system processor keeps a record of the first address used in the cine buffer and subtracts the first address from the last address used to store an image frame in the cine buffer for an examination. The result is the number of memory addresses used to store the image frames in the cine buffer. An index into the cine buffer for the equally spaced image frames can be determined by the processor based on the first and last address, the number of memory addresses used by each image frame (assumed to be the same for each image frame) and the number of image frames desired to be presented.

In an alternative embodiment, the system processor 116 or other image processor analyzes the image frames stored in the cine buffer for one or more image frames that bear the closest resemblance to one or more target image frames associated with the examination being performed. In one embodiment, the system processor 116 is configured to execute program instructions to determine the number and type of image frames that are required by a particular type of examination from the knowledge base 170. The system processor then recalls one or more target image frames from the image database 180. Image frames in the cine buffer 120 are then compared to the target image frames to find the closest matches. The closest matches are then presented to the operator for approval.

There are a number of well-known image comparison techniques that can be used by the system processor to compare the image frames in the cine buffer with a target image frame. For example, a simple least squares comparison of the pixel brightness for the pixels in an image frame stored in the cine buffer memory and the target image frames can be used. In another embodiment, image frames can be classified by a histogram of brightness values and a comparison made to determine if the two histograms are similar. In yet another embodiment, two-dimensional Fourier transforms of the image frames are compared to determine how similar the image frames are. Other more complicated and well-known image comparison algorithms such as SIFT, PCA-SIFT and SURF could also be used to compare image frames. Image frames that most closely match the target image frames are selected and presented to the operator to approve or reject.

If an examination requires imaging different portions of the body, then the proposed image frames can be selected by the system processor based on how different the image frames are. For example, if an examination is to image the heart, lungs and liver, the procedure begins by obtaining image frames of the heart which should look fairly similar to each other. Once the operator begins imaging another part of the body such as the lungs, the image frames will look quite different from the image frames of the heart. The system processor therefore executes program instructions that compare sequential frames from the cine buffer and selects an image frame that differs significantly from a previous frame. The sequential image frame comparison may also be used in conjunction with a comparison against one or more target image frames recalled from the image database. For example, if an examination starts with imaging the heart and then moves to the lungs, the first frame that looks substantially different than the image frames of the heart may be compared to a target image frame of a lung. Subsequent frames can also be compared to the target image frame of the lung so that not every frame in the cine buffer need be compared with the target frame.

In yet another embodiment, the ultrasound system stores locally or recalls from a remote computer system, image frames that were selected by the operator on one or more previous occasions when the operator performed the same type of ultrasound examination that is currently being performed. The previously selected image frames are then used as target image frames for comparison against the image frames that are stored in the cine buffer. Those image frames that bear the closest resemblance to the previously selected target image frames are presented by the system processor for the operator to approve or reject.

In yet another embodiment, the system processor analyzes the image frames stored in the cine buffer for the presence of an object. The object can be an anatomical structure such as a particular portion of the heart, a particular organ or portion thereof (e.g. a liver) whose ultrasound image can be characterized by shape or by echo characteristics. Alternatively, the object can be a surgical instrument, such as a needle, or drug such as anesthetic, that can be detected in an image based on its shape or echo characteristics. For example, needle detection typically involves the detection of a bright reflector in a linear path within an image frame. The image frames in the cine buffer that contain the object are presented to the operator for approval or rejection.

In yet another embodiment, image frames are selected that meet some pre-defined image criteria. For example if an image of a heart valve needs to occupy a certain size in an image frame, then the image processor can analyze the images for the presence of the heart valve and can calculate whether the size of the heart valve in the image meets the predefined criteria. If an image frame meets both these criteria, the image frame is presented to the operator for approval or rejection. Other image criteria such a Doppler measurement that exceeds or is below a threshold could also be used.

In yet another embodiment, image frames are selected that were obtained with some defined operating criteria of the ultrasound machine. For example, image frames may be required where the image depth is between 5 and 7 cm. If the image frames are recorded with meta data in the cine buffer that indicates the depth of focus, then the system processor, or other image processor, can select one or more image frames that were obtained at the desired depth of focus. Other imaging parameters can include power level of signals applied to the transducer or other characteristics that can be modified to obtain an image frame and are recorded by the ultrasound system.

Once the proposed image frames are identified, the image frames are presented to the operator. The operator can accept or reject the proposed image frames for inclusion in a patient or billing report. If one or more of the proposed the frames are rejected, the operator can select another frame(s) by browsing the frames stored in the cine buffer. As indicated above, in one embodiment, the operator can jump to a location in the cine buffer by selecting a proposed frame in order to view the image frames stored before and after the proposed image frame. The ultrasound system also provides the operator with one or more hardware or software controls by which the operator can scroll through the cine buffer in a manner similar to a video (e.g. run, pause, stop, fast forward, rewind etc.) and a control to select an image frame.

Image frames that are accepted are marked by the system processor for inclusion in a patient or other report. Marking can be performed in a variety of manners such as by changing meta data associated with an image frame. Alternatively, the system processor can keep a list of image frames associated with a particular examination that are to be included in a patient or other report.

In one embodiment, once the selected image frames have been identified, the image frames (which may or may not include the non-selected image frames) can be stored in the memory 126 or other memory for archival purposes. In one embodiment, the selected image frames are stored with a greater resolution than the non-selected frames to preserve as much detail as possible in the selected frames.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus.

A computer storage medium can be, or can be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium also can be, or can be included in, one or more separate physical components or media (e.g., multiple CDs, disks, or other storage devices). The operations described in this specification can be implemented as operations performed by a data processing apparatus on data stored on one or more computer-readable storage devices or received from other sources.

The term "processor" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus also can include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a imaging system having a display device, e.g., an LCD (liquid crystal display), LED (light emitting diode), or OLED (organic light emitting diode) monitor, for displaying information to the operator and a keyboard and a pointing device, e.g., a mouse or a trackball, by which the operator can provide input to the computer. In some implementations, a touch screen can be used to display information and to receive input from a user. Other kinds of devices can be used to provide for interaction with a operator as well; for example, feedback provided to the operator can be any form of sensory feedback, e.g., visual feedback, auditory feedback, or tactile feedback; and input from the operator can be received in any form, including acoustic, speech, or tactile input. In addition, a computer can interact with an operator by sending documents to and receiving documents from a device that is used by the user; for example, by sending web pages to a web browser on a user's client device in response to requests received from the web browser.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

We claim:

1. An ultrasound imaging system comprising:
   a transducer that is configured to transmit ultrasound signals to and receive ultrasound signals from a region of interest;
   receive circuitry that is configured to convert the received ultrasound signals into image frames of ultrasound data for display to an operator;
   a display for displaying the image frames of ultrasound data;
   a cine buffer in which a first plurality of image frames of ultrasound data produced during an examination time are stored; and
   a processor that is configured to determine a second plurality of the image frames from the first plurality that are stored at equally spaced time intervals within the cine buffer during the examination time, wherein the processor is configured select one or more image frames from the cine buffer for presentation to the operator based on the first plurality of the image frames, and to receive confirmation from the operator whether to mark one or more of the selected image frames for inclusion in a patient record or other report, the one or more image frames being selected as a result of the processor analyzing the one or more image frames without input from the operator.

2. The ultrasound imaging system of claim 1, further comprising a memory that stores one or more target image frames that are associated with particular examination types and wherein the processor is configured to compare the image frames that are stored in the cine buffer to one or more target images associated with a type of examination being performed by the operator.

3. The ultrasound imaging system of claim 1, wherein the processor is configured to receive a selection of an image frame by the operator and to
   display image frames that were recorded in the cine buffer before and/or after the selected image frame.

4. The ultrasound imaging system of claim 1, wherein the processor is configured to analyze image frames in the cine buffer and select for presentation one or more image frames that differ from an image frame that was stored before the selected image frame.

5. The ultrasound imaging system of claim 1, wherein the processor is configured to compare image frames in the cine buffer with one or more target image frames that the operator has previously selected when performing a type of examination and to select one or more image frames for presentation that match the target image frames.

6. The ultrasound imaging system of claim 1, wherein the processor is configured to analyze the image frames stored in the cine buffer for the presence of a defined feature and to present one or more image frames that contain the defined feature.

7. The ultrasound imaging system of claim 6, wherein the defined feature is an anatomical feature.

8. The ultrasound imaging system of claim 6, wherein the defined feature is a surgical instrument.

9. The ultrasound imaging system of claim 6, wherein the defined feature is a needle.

10. The ultrasound imaging system of claim 6, wherein the defined feature is a drug being delivered around a target location.

\* \* \* \* \*